US005761257A

United States Patent [19]
Toth et al.

[11] Patent Number: 5,761,257
[45] Date of Patent: Jun. 2, 1998

[54] NORMALIZING PROJECTION DATA IN A COMPUTED TOMOGRAPHY SYSTEM

[75] Inventors: Thomas Louis Toth, Brookfield; Jonathan Richard Schmidt, Wales, both of Wis.

[73] Assignee: General Electric Company, Milwaukee, Wis.

[21] Appl. No.: 759,133

[22] Filed: Dec. 2, 1996

[51] Int. Cl.⁶ .................................................. G01N 23/00
[52] U.S. Cl. ...................................... 378/19; 378/4
[58] Field of Search .............................. 378/19, 4, 108, 378/207

[56] References Cited

U.S. PATENT DOCUMENTS 5,430,785  7/1995  Pfoh et al. ............................ 378/207

Primary Examiner—Don Wong
Attorney, Agent, or Firm—John S. Beulick; John H. Pilarski

[57] ABSTRACT

The present invention, in one form, is a method for detecting reference channel blockage in a computed tomography system. The system includes an x-ray source, a detector and a reference channel. When scanning an object of interest, the x-ray source is supplied with an x-ray source current and projects an x-ray beam toward the detector and the reference channel. The detector, when impinged by the x-ray beam, generates projection data for reconstructing an image of the object of interest. The reference channel is configured to generate an actual reference channel signal when impinged by the x-ray beam. An expected reference signal is determined in accordance with the x-ray source current. The expected reference signal is then utilized to normalize the projection data.

18 Claims, 5 Drawing Sheets

Subtract Offsets & Form Left And Right Gain Normalized Averages

$R'_i(\theta_j) = R_i(\theta_j) - O_i$ $i$ reference channel index $0..5$ $j$ view index $R_i(\theta_j)$ Raw ref channel data $O_i$ Offset ref channel Data $$L\_ave(\theta_j) = \sum_{i=1,2} \frac{R'_i(\theta_j)}{2} \qquad R\_ave(\theta_j) = \sum_{i=3,5} \frac{R'_i(\theta_j)}{3}$$

Test For Absolute Blockage on Both Sides if $R'_i(\theta_j) \leq (mA)(ThA)(M_i)$ Then SUBSTITUTE ABSOLUTE $ThA = 0.8(1 - \text{Modulation Index})$ $$M_i = \frac{\sum_{\theta_j=0,n-1} R'_i(\theta_j)}{(mA)(n)}$$

mA normalized reference value determined during Fast Cal (A)

FIG. 3A

NORMALIZING PROJECTION DATA IN A COMPUTED TOMOGRAPHY SYSTEM

FIELD OF THE INVENTION

This invention relates generally to computed tomography (CT) imaging and more particularly, to normalizing projection data obtained during CT scans.

BACKGROUND OF THE INVENTION

In at least one known CT system configuration, an x-ray source projects a fan-shaped beam which is collimated to lie within an X–Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles during one revolution of the x-ray source and detector. In an axial scan, the projection data is processed to construct an image that corresponds to a two dimensional slice taken through the object. One method for reconstructing an image from a set of projection data is referred to in the art as the filtered backprojection technique. This process converts the attenuation measurements from a scan into integers called "CT numbers" or "Hounsfield units", which are used to control the brightness of a corresponding pixel on a cathode ray tube display.

To reduce the total scan time required for multiple slices, a "helical" scan may be performed. To perform a "helical" scan, the patient is moved while the data for the prescribed number of slices is acquired. Such a system generates a single helix from a one fan beam helical scan. The helix mapped out by the fan beam yields projection data from which images in each prescribed slice may be reconstructed. An image reconstruction algorithm which may be utilized in reconstructing an image from data obtained in a helical scan is described, for example, in U.S. patent application Ser. No. 08/436,176, filed May 9, 1995, and assigned to the present assignee. In addition to reduced scanning time, helical scanning provides other advantages such as better control of contrast, improved image reconstruction at arbitrary locations, and better three-dimensional images.

X-ray sources typically include x-ray tubes, which emit the x-ray beam at a focal spot. X-ray intensity, or dosage, is related directly to the x-ray tube current which flows in the x-ray tube. X-ray intensity also effects image quality. Particularly, the signals generated by the detector elements are directly related to the intensity of the x-ray beam. A high intensity x-ray beam, for example, generates a strong detector element signal. Conversely, a low intensity x-ray beam generates a weak detector element signal.

X-ray tube current, and thus x-ray intensity, often varies during a scan to prevent a patient, as well as the detector elements, from receiving excessive x-ray dose. One such variable x-ray tube current system is described in U.S. Pat. No. 5,379,333, entitled "Variable Dose Application By Modulation of X-Ray Tube Current During CT Scanning", which is assigned to the present assignee. Varying x-ray tube current during a scan permits high x-ray intensities to be generated while scanning high attenuation regions of a patient, and low x-ray intensities to be generated while scanning low attenuation regions of the patient. The different intensities, as discussed above, generate different strength detector element signals.

To maintain image quality regardless of x-ray intensity, therefore, detector signals, i.e., projection data, are normalized before generating an image. Particularly, and for each view, projection data is normalized relative to the intensity of the x-rays impinging upon the detector elements. To normalize the projection data, it is known to utilize reference channels on the detector array. The reference channels are positioned at either end of the detector array so that they generally are unobstructed by the object, i.e., the reference channels receive non-attenuated x-rays. Each reference channel, similar to the detector elements, produces a separate electrical signal that is a measurement of the beam attenuation at the reference channel location. The signals generated by the reference channels are then utilized to normalize the signals, i.e., projection data, generated across the detector array.

Reference channels, however, often become blocked during a scan. Particularly, the object being imaged or some other object often obscures, or blocks, the reference channels, thus causing the reference channels to receive attenuated x-rays. Reference channels, in such circumstances, generate a corrupt normalization value, which degrades the image quality. Specifically, incorrect normalization causes streaks and artifacts to appear in displayed images.

Methods have been developed to detect reference channel blockages. Such methods, upon detecting a reference channel blockage, determine an appropriate normalization value and utilize the determined value to normalize the projection data. While such methods generally are satisfactory, such methods typically are complex, and require significant computational time and resources. The known methods are particularly complex and burdensome when used in connection with variable signal intensity scans, also referred to herein as variable x-ray tube current scans.

It is desirable, of course, to accurately normalize projection data during stable and variable x-ray tube current scans. It also is desirable to more efficiently normalize projection data without increasing the costs of the CT system.

SUMMARY OF THE INVENTION

These and other objects may be attained in a system which, in one embodiment, utilizes x-ray tube current to normalize the projection data. Particularly, and in one form, the system determines an expected reference channel signal Sx in accordance with the supplied x-ray tube current. For each view, the determined expected reference channel signal Sx is used to normalize the projection data. More particularly, and in accordance with one embodiment, the determined expected reference channel signal Sx is compared to an actual reference channel signal Sr. If the actual reference channel signal Sr is above a threshold value, then projection data is normalized using the actual reference channel signal Sr. Alternatively, and if the actual reference channel signal Sr is below a threshold value, then projection data is normalized using the determined expected reference channel signal Sx.

The system described above accurately normalizes projection data acquired during scans including variable x-ray source current scans. The system also is substantially simple, and significantly reduces computation costs associated with detecting reference channel blockages.

DETAILED DESCRIPTION OF THE DRAWINGS

Figure 1:
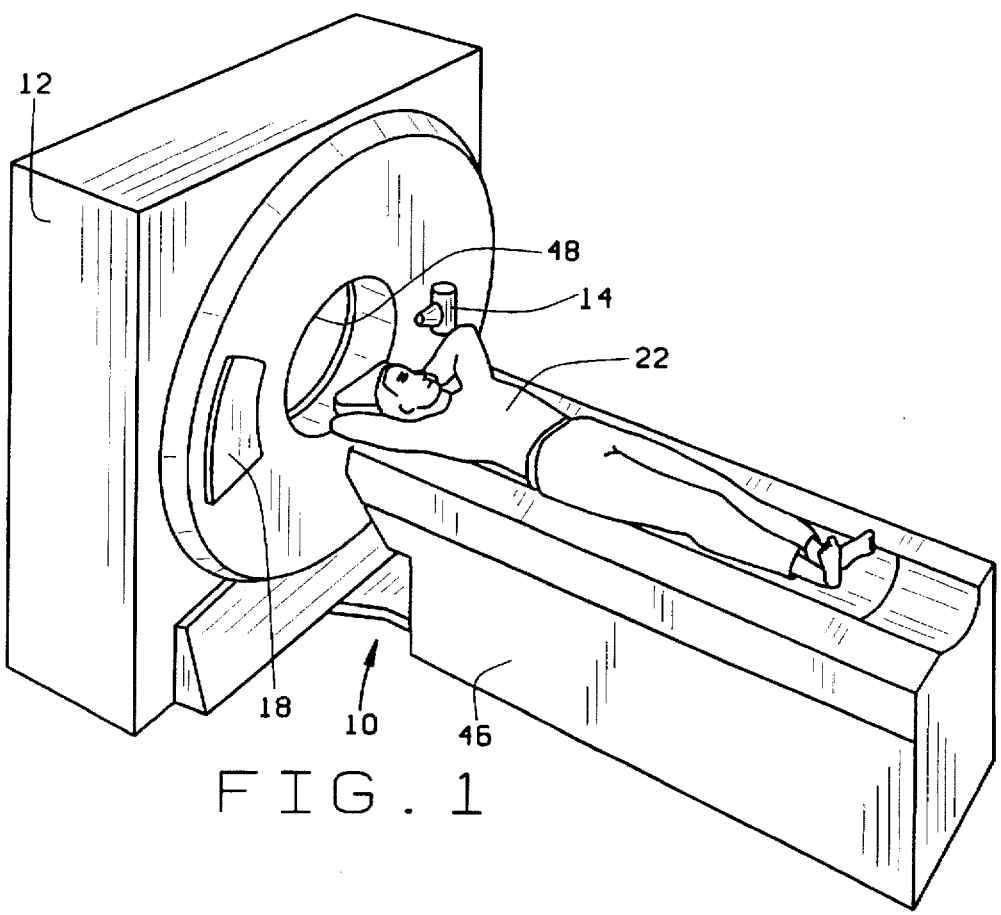
FIG. 1 is a pictorial view of a CT imaging system.
Figure 2:
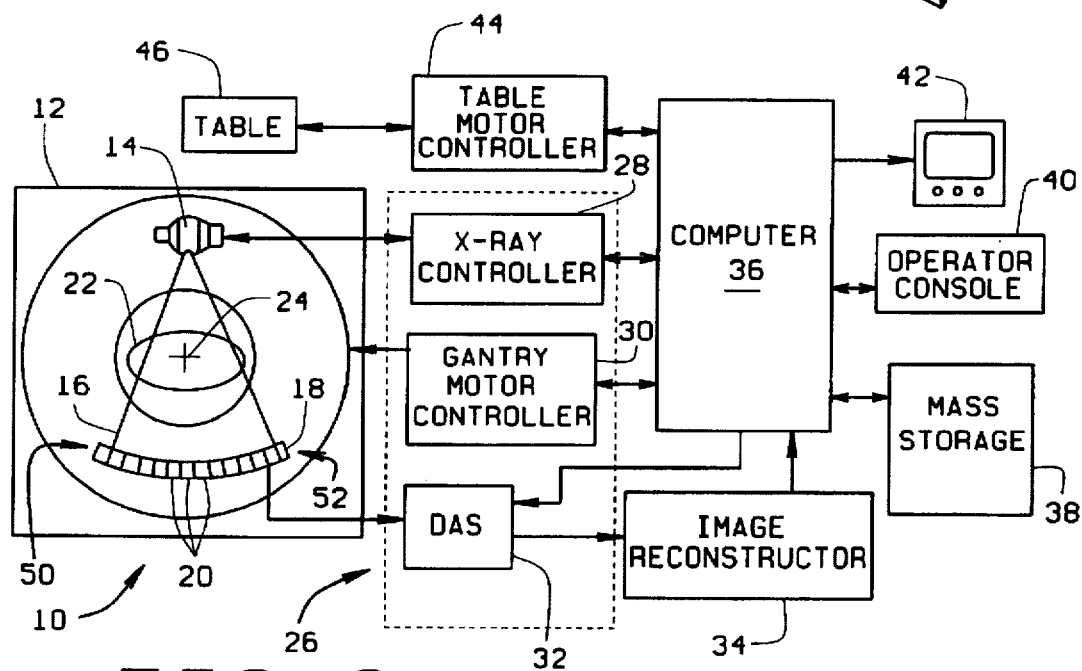
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. Gantry 12 has an x-ray source, or tube 14 that projects a beam of x-rays 16 toward a detector array 18 on the opposite side of gantry 12. Detector array 18 is formed by detector elements 20 which together sense the projected x-rays that pass through a medical patient 22. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

Detector array 18 further includes at least one reference channel (not shown in FIGS. 1 and 2) for normalizing the projection data. Each reference channel typically is positioned adjacent detector array 18. Particularly, each reference channel is positioned adjacent one of the ends 50 and 52 of detector array 18 so that the reference channel receives nonattenuated x-rays from x-ray beam 16. Each reference channel, in response to the x-rays, generates a reference signal which is used to normalize the projection data.

However, as explained above, the reference channels are often blocked, for example, by patient 22, and thus receive attenuated x-rays. In such circumstances, the reference channels generate a corrupt normalization value, which degrades image quality. To reduce generation of corrupt normalization values, it therefore is desirable to detect reference channel blockage. It also is desirable to generate appropriate reference signals when reference channels are blocked.

Figure 3B:
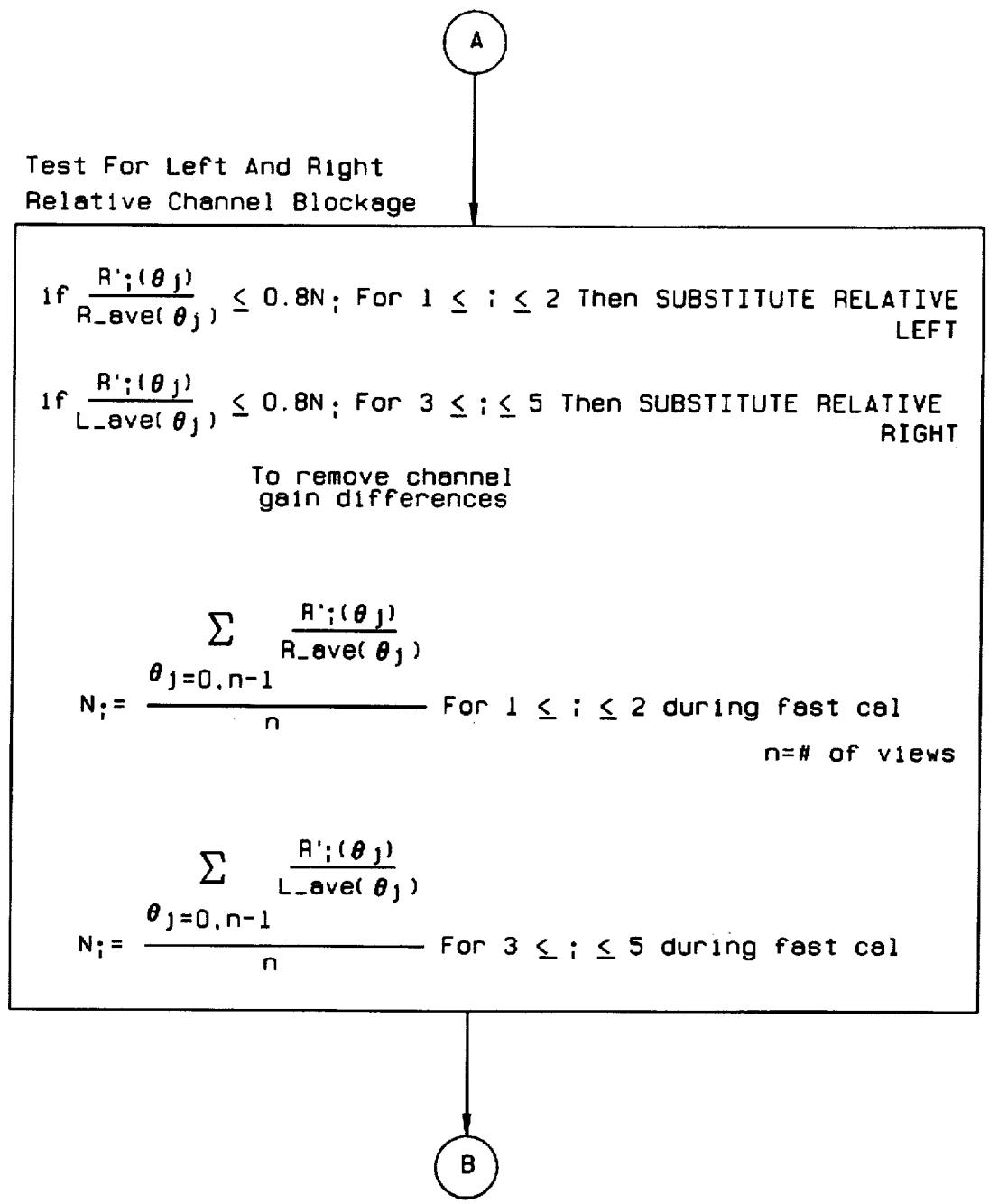
FIG. 3 is a flow chart illustrating a sequence of process steps in accordance with a known algorithm for detecting reference channel blockage and producing an appropriate reference signal.
Figure 3C:
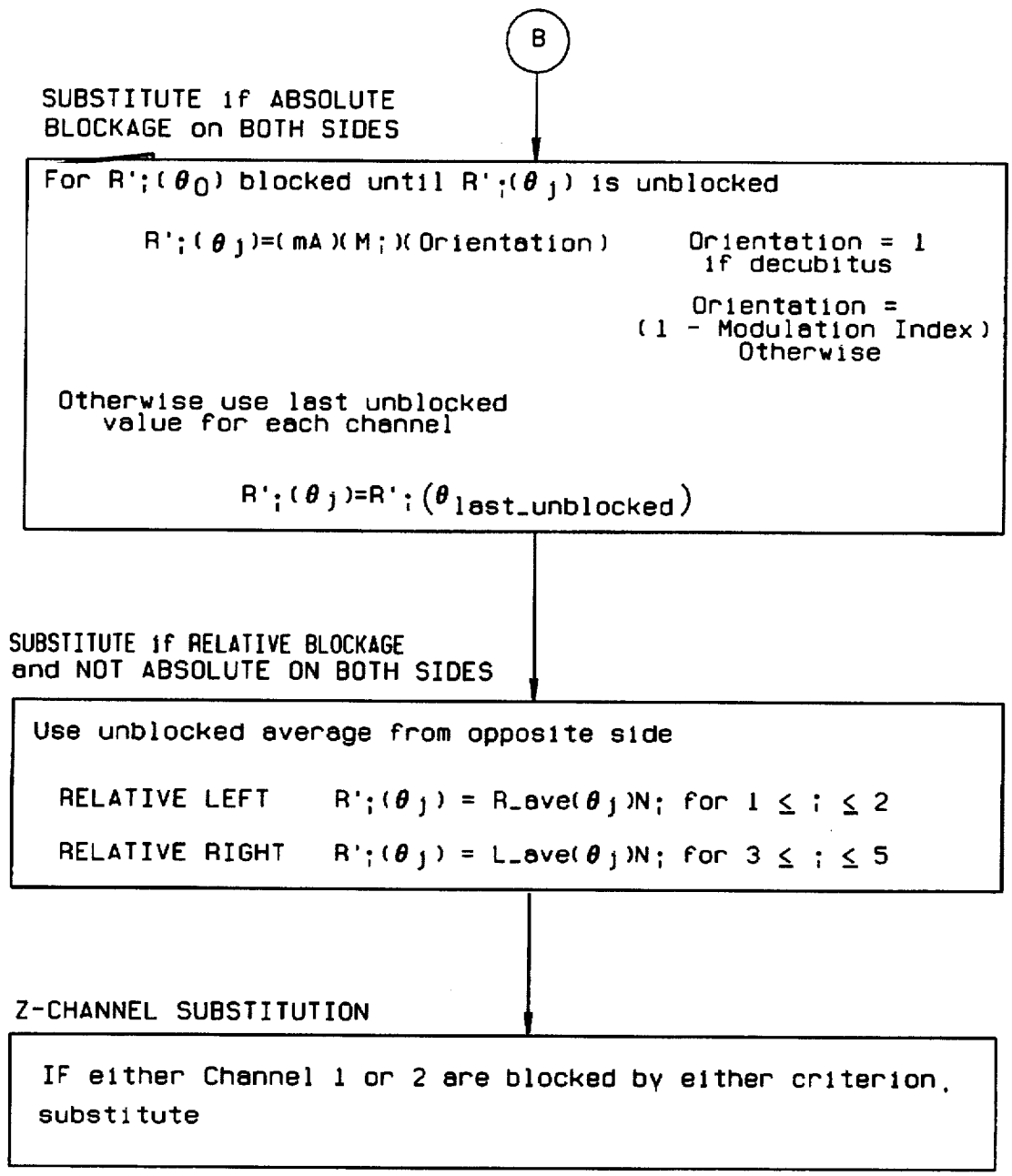

FIG. 3 is a flow chart illustrating a sequence of process steps in accordance with a known algorithm for detecting reference channel blockage and producing an appropriate reference signal. This algorithm typically is implemented in computer 36, although it also may be implemented in DAS 32. The algorithm includes six distinct process steps: 1) subtracting offsets and forming left and right gain normalized averages, 2) testing for absolute blockage on both sides of the detector array, 3) testing for left and right relative channel blockage, 4) substituting for absolute blockage on both sides, 5) substituting for relative channel blockage, i.e., both sides are not absolutely blocked, and 6) z-channel substitution. In FIG. 3, the j and i indexes represent view and channel indexes, respectively.

The first step of subtracting offsets and forming left and right gain normalized averages is shown in FIG. 3. Similarly, the second step of testing for absolute blockage on both sides of the detector array is shown in FIG. 3. The third step of testing for left and right relative channel blockage also is shown in FIG. 3.

If absolute blockage is detected, an appropriate substitute reference signal is generated in accordance with step 4, as shown in FIG. 3. However, if relative channel blockage is detected, and both sides are not absolutely blocked, a different appropriate substitute reference signal is generated in accordance with step 5, as shown in FIG. 3. The appropriate substitute reference signal generated in either step 4 or step 5 is then substituted, in step 6, for the blocked reference signal.

The above-described algorithm, as shown, is cumbersome and complex. Furthermore, significant computational costs and time are expended during algorithm implementation. These computational costs and time significantly increase when the algorithm is implemented in connection with variable x-ray tube current scans.

In accordance with one embodiment of the present invention, x-ray source current is used to both determine reference channel blockage and provide an acceptable substitute reference signal. The algorithm is not directed to any particular scanning system such as non-variable x-ray tube current and variable x-ray tube current systems. Rather, the present algorithm may be used in conjunction, albeit during a scan, with such systems. It should also be understood that the present algorithm may be used in imaging systems having x-ray sources other than x-ray tubes. It should be further understood that the current algorithm would be implemented in computer 36 and would control, for example, DAS 32 to use a desired reference channel signal to normalize projection data. Other implementations, of course, are possible.

Figure 4:
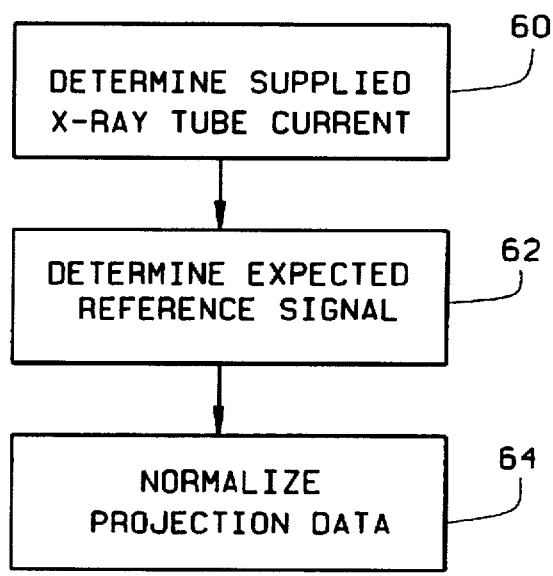
FIG. 4 is a flow chart illustrating a sequence of process steps in accordance with one embodiment of the present invention.

FIG. 4 is a flow chart illustrating a sequence of process steps in accordance with one embodiment of the present invention. For each view, the x-ray tube current supplied during that view is determined 60. The determined x-ray tube current, as described above, is related to the intensity of x-ray beam 16 generated during the view. To obtain the supplied x-ray tube current, and for example, x-ray controller 28 (FIG. 1) is configured to generate a signal representative of x-ray tube current. In addition, computer 36 (FIG. 1) is coupled to x-ray controller 28 so that it receives the signal from x-ray controller 28 via an input (not shown) and identifies an x-ray tube current measurement value. X-ray tube current determination also may be obtained by other implementations.

An expected reference signal Sx is then determined 62 using the determined x-ray tube current. In a CT system 10 where the voltage supplied to x-ray tube 14 is stable, reference signal Sx is determined in accordance with the equation:

$$Sx = mAm * nrm, \quad (1)$$

where:

mAm is the supplied x-ray tube current; and nrm is a calibrated reference channel signal factor. Specifically, nrm is calibrated so that:

$$nrm = Sr/mAm, \quad (2)$$

where Sr is the actual reference channel signal generated by the reference channels. nrm may be calibrated, for example, during air calibration of CT system 10. Calibrating nrm during CT system air calibration is not believed to add computational time or expenses to air calibration.

The supplied x-ray tube current, mAm, is filtered prior to determining expected reference signal Sx. Filtration may be performed by known methods, and enable the value of mAm to approximately match a response of actual reference channel signal Sr.

After determining expected reference signal Sx, the projection data is normalized 64. Particularly, determined expected reference signal Sx is used to normalize the projection data. More specifically, a threshold factor Th is identified and multiplied to expected reference signal Sx to generate a threshold value Th*Sx. Threshold factor Th, in one embodiment, is 0.8, and may be stored, for example, in the memory of computer 36. Actual reference channel signal Sr is compared to threshold value Th*Sx. If Sr is less than Th*Sx, then the reference channels are assumed to be blocked, and actual reference signal Sr thus assumed to be incorrect. Accordingly, Sx, rather than Sr, is utilized to normalize the projection data. Normalization techniques using a reference signal are known.

Alternatively, if Sr is greater than Th*Sx, then the reference channels are assumed to clear, and actual reference channel signal Sr thus substantially correct. Accordingly, and when Sr is greater than Th*Sx, the projection data is normalized by utilizing actual reference channel signal Sr in accordance with known projection data normalization methods.

The above-described algorithm provides a substantially simple and efficient method for accurately detecting reference channel blockage and providing an acceptable substitute reference signal. The algorithm also may be implemented with fewer computational costs than those required with known algorithms.

In another embodiment of the present invention, and where the voltage supplied to x-ray tube 14 varies, reference signal Sx is determined in accordance with the equation:

$$Sx = mAam * mKv^2 * nrm, \quad (3)$$

where:

mAm is the supplied x-ray tube current;

mKv is the voltage supplied to the x-ray tube; and nrm is a calibrated reference channel signal factor.

The exponent of mKv, i.e., 2, is selected in accordance with the voltage supplied by, for example, x-ray controller 28 (FIG. 1). Particularly, the exponent may be empirically derived to be accurate in the vicinity of an expected x-ray tube voltage.

The value nrm is calibrated so that:

$$nrm = Sr/(mAm * mKv^2). \quad (4)$$

Determined expected reference signal Sx is then used to normalize the projection data. Particularly, a threshold factor Th is identified and multiplied to expected reference signal Sx to generate a threshold value Th*Sx. Threshold factor Th again may, for example, be 0.8. Actual reference channel signal Sr is compared to threshold value Th*Sx. If Sr is less than Th*Sx, then the reference channels are assumed to be blocked, and actual reference signal Sr thus incorrect. Accordingly, Sx is utilized to normalize the projection data.

Alternatively, if Sr is greater than Th*Sx, then the reference channels are assumed to clear, and actual reference channel signal Sr thus substantially correct. Therefore, in such circumstance, actual reference channel signal Sr is utilized to normalize the projection data.

The above-described algorithm provides a substantially simple and efficient method for accurately detecting reference channel blockage and providing an acceptable substitute reference signal even where x-ray tube voltage varies. This algorithm also may be implemented with fewer computational costs than those required with known algorithms.

In yet another embodiment of the present invention, expected reference signal Sx always is used to normalize the projection data. In this embodiment, the step of comparing Sx to an actual reference channel signal Sr is eliminated, thus further increasing the efficiency and accuracy of normalizing projection data.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. For example, the CT system described herein is a "third generation" system in which both the x-ray source and detector rotate with the gantry. Many other CT systems including "fourth generation" systems wherein the detector is a full-ring stationary detector and only the x-ray source rotates with the gantry, may be used. Moreover, the x-ray tube current may be determined by, for example, DAS 32 rather than computer 36. Similarly, the calculations may be implemented in DAS 32 rather than computer 36. In addition, the threshold factor Th can be other than 0.8. Accordingly, the spirit and scope of the invention are to be limited only by the terms of the appended claims.

What is claimed is:

1. A method for detecting reference channel blockage in a computed tomography system including an x-ray source for emitting an x-ray beam and scanning an object of interest, the system using projection data to reconstruct an image of the object, the system further including a reference channel configured to generate an actual reference channel signal when impinged by the x-ray beam, said method comprising the steps of:

determining a supplied x-ray source current;

determining an expected reference signal; and normalizing the projection data using the expected reference signal.

2. A method in accordance with claim 1 wherein determining the expected reference signal comprises the step of determining a reference channel signal factor.

3. A method in accordance with claim 2 further comprising the step of comparing the expected reference signal to the actual reference channel signal.

4. A method in accordance with claim 2 wherein determining the expected reference signal further comprises the steps of:

calibrating the reference channel signal factor; and multiplying the calibrated reference channel signal factor and the supplied x-ray source current.

5. A method in accordance with claim 4 wherein calibrating the reference channel signal factor is performed in accordance with:

$$nrm = Sr/mAm,$$

where:

Sr is the actual reference channel signal;

mAm is the supplied x-ray tube current; and nrm is a calibrated reference channel signal factor.

6. A method in accordance with claim 5 wherein determining the expected reference channel signal is performed in accordance with:

$$Sx = mAm * nrm,$$

where:

Sx is the expected reference channel signal;

mAm is the supplied x-ray source current; and nrm is the calibrated reference channel signal factor.

7. A method in accordance with claim 4 wherein calibrating the reference channel signal factor is performed in accordance with:

$$nrm = Sr/(mAm * mKv^2),$$

where:

Sr is the actual reference channel signal;

mAm is the supplied x-ray source current;

mKv is the voltage supplied to the x-ray source; and nrm is the calibrated reference channel signal factor.

8. A method in accordance with claim 7 wherein determining the expected reference signal further comprises the step of determining a voltage supplied to the x-ray source, and wherein determining the expected reference signal is performed in accordance with:

$$Sx = mAm * mKv^2 * nrm,$$

where:

Sx is the expected reference channel signal;

mAm is the supplied x-ray tube current;

mKv is the voltage supplied to the x-ray tube; and nrm is a calibrated reference channel signal factor.

9. A method in accordance with claim 8 further comprising the steps of:

identifying a threshold factor;

multiplying the threshold factor and the expected reference signal to generate a threshold value; and comparing the generated threshold value to the actual reference channel signal.

10. A system for detecting reference channel blockage in a computed tomography system, the computed tomography system including an x-ray source for emitting an x-ray beam and scanning an object of interest, the computed tomography system using projection data to reconstruct an image of the object, the computed tomography system further including at least one reference channel, the reference channel configured to generate an actual reference channel signal when impinged by the x-ray beam, said system configured to:

determine a supplied x-ray source current;

determine an expected reference signal; and normalize the projection data using the expected reference signal.

11. A system in accordance with claim 10 further configured to determine a reference channel signal factor.

12. A system in accordance with claim 11 further configured to compare the expected reference signal to the actual reference channel signal.

13. A system in accordance with claim 12 further configured to:

identify a threshold factor;

multiply the threshold factor and the expected reference signal to generate a threshold value; and compare the generated threshold value to the actual reference channel signal.

14. A system in accordance claim 11 wherein to determine the expected reference signal, said system is further configured to calibrate the reference channel signal factor.

15. A system in accordance with claim 14 wherein the calibrated reference channel signal factor is:

$$nrm = Sr/mAm,$$

where:

Sr is the actual reference channel signal;

mAm is the supplied x-ray tube current; and nrm is a calibrated reference channel signal factor.

16. A system in accordance with claim 15 wherein the expected reference signal is:

$$Sx = mAm * nrm,$$

where:

Sx is the expected reference channel signal;

mAm is the supplied x-ray source current; and nrm is the calibrated reference channel signal factor.

17. A system in accordance with claim 14 wherein the calibrated reference channel signal factor is:

$$nrm = Sr/(mAm * mKv^2),$$

where:

Sr is the actual reference channel signal;

mAm is the supplied x-ray source current;

mKv is the voltage supplied to the x-ray source; and nrm is the calibrated reference channel signal factor.

18. A system in accordance with claim 17 wherein the expected reference signal is:

$$Sx = mAm * mKv^2 * nrm,$$

where:

Sx is the expected reference channel signal;
mAm is the supplied x-ray tube current;
mKv is a voltage supplied to the x-ray tube; and
nrm is a calibrated reference channel signal factor.

* * * * *